(12) United States Patent
Seitz et al.

(10) Patent No.: US 10,130,922 B2
(45) Date of Patent: Nov. 20, 2018

(54) RECEPTACLE COMPRISING A SHAFT HOUSING

(71) Applicant: Sartorius Stedim Biotech GmbH, Goettingen (DE)

(72) Inventors: Reiner Seitz, Helsa (DE); Rainer Salzmann, Melsungen (DE); Thomas Regen, Goettingen (DE); Matthias Hielscher, Hessisch Lichtenau (DE); Bernward Husemann, Goettingen (DE); Stefan Zeuch, Goettingen (DE); Ute Husemann, Goettingen (DE); Gerhard Greller, Goettingen (DE)

(73) Assignee: SARTORIUS STEDIM BIOTECH GMBH, Goettingen (DE)

( * ) Notice: Subject to any disclaimer, the term of this patent is extended or adjusted under 35 U.S.C. 154(b) by 335 days.

(21) Appl. No.: 14/900,625

(22) PCT Filed: May 28, 2014

(86) PCT No.: PCT/EP2014/061025
§ 371 (c)(1),
(2) Date: Dec. 22, 2015

(87) PCT Pub. No.: WO2015/022099
PCT Pub. Date: Feb. 19, 2015

(65) Prior Publication Data
US 2016/0151749 A1    Jun. 2, 2016

(30) Foreign Application Priority Data

Jun. 26, 2013 (DE) .................. 10 2013 106 680

(51) Int. Cl.
*B01F 7/00*     (2006.01)
*B01F 15/00*    (2006.01)
(Continued)

(52) U.S. Cl.
CPC ...... *B01F 7/00683* (2013.01); *B01F 15/0085* (2013.01); *B01F 15/00441* (2013.01);
(Continued)

(58) Field of Classification Search
CPC .......... B01F 15/00441; B01F 15/00707; B01F 15/0085; B01F 2015/00084;
(Continued)

(56) References Cited

U.S. PATENT DOCUMENTS 5,509,667 A * 4/1996 Klein .................... F16C 27/066
                                                        277/565
2005/0239199 A1* 10/2005 Kunas .................... B01F 7/001
                                                        435/297.1
(Continued)

FOREIGN PATENT DOCUMENTS

DE    10 2008 010 427    8/2009
DE    10 2009 018 209    10/2009

OTHER PUBLICATIONS

English Translation of International Preliminary Report on Patentability dated Dec. 29, 2015.
International Search Report.

*Primary Examiner* — Nathan A Bowers
*Assistant Examiner* — Lydia Edwards
(74) *Attorney, Agent, or Firm* — Gerald E. Hespos; Michael J. Porco; Matthew T. Hespos

(57) ABSTRACT

A receptacle has a wall defining a receptacle interior and a shaft housing for guiding a shaft through the wall into the receptacle interior. The shaft housing defines an annular cap with spaced apart inner and outer walls connected by an inner end face facing the receptacle interior. A shaft guide part has an end facing the receptacle interior and an outer surface that defines a gap relative to the inner wall of the shaft housing. The shaft guide part has an annular wall spaced apart from and parallel to its outer surface. The
(Continued)

annular wall extends over the free end of the inner wall of the shaft housing and is sealed to the inner and outer walls of the shaft housing by at least one seal each. The shaft guide part is mounted in the shaft housing by a radial ball bearing and by an axial ball bearing.

12 Claims, 3 Drawing Sheets

(51) Int. Cl.
       *C12M 1/00*       (2006.01)
       *C12M 1/06*       (2006.01)
       *C12M 1/12*       (2006.01)
       *F16C 19/54*      (2006.01)
       *F16J 15/00*      (2006.01)
       *F16C 33/76*      (2006.01)

(52) U.S. Cl.
    CPC ....... *B01F 15/00707* (2013.01); *C12M 23/26* (2013.01); *C12M 23/28* (2013.01); *C12M 27/02* (2013.01); *C12M 37/04* (2013.01); *F16C 19/545* (2013.01); *F16J 15/002* (2013.01); *B01F 2015/0011* (2013.01); *B01F 2015/00084* (2013.01); *F16C 33/76* (2013.01)

(58) Field of Classification Search
    CPC ......... B01F 2015/0011; B01F 7/00683; C12M 23/26; C12M 23/28; C12M 27/02; C12M 37/04; F16C 19/545; F16C 33/76; F16J 15/002; G06F 3/0416
    See application file for complete search history.

(56) References Cited

U.S. PATENT DOCUMENTS

| | | |
|---|---|---|
| 2006/0280028 A1 | 12/2006 | West et al. |
| 2011/0003374 A1 | 1/2011 | Van Den Boogaard et al. |
| 2011/0026360 A1* | 2/2011 | Greller ................ B01F 7/00633 366/308 |

* cited by examiner

RECEPTACLE COMPRISING A SHAFT HOUSING

BACKGROUND

1. Field of the Invention

The invention relates to a receptacle comprising a shaft housing for guiding a shaft through a wall into the receptacle interior, the shaft being mounted in the shaft housing via a shaft guide part by way of ball bearings and being sealed relative to the shaft housing by means of seals.

2. Description of the Related Art

A receptacle comprising a shaft housing for guiding a shaft through a wall into the receptacle interior is known in the prior art from DE 10 2008 010 427 B4, with the shaft being mounted in the shaft housing via a shaft guide part by way of ball bearings and being sealed relative to the shaft housing by means of seals.

A disadvantage of the receptacle known in the prior art, which has in principle proven to be especially useful for bioreactors with flexible walls, is that wear debris from the sealing lips can penetrate into the receptacle interior. As the receptacle moves, the seals may be subject to uneven stress.

Furthermore, a shaft housing for guiding a shaft through a wall into a receptacle interior is known in the prior art from US 2006/0280028 A1, in which a shaft guide part in the shaft housing is mounted by means of two radial ball bearings. The shaft guide part has a level collar arranged radially, which can be sealed at both sides with seals.

A disadvantage of this configuration is that seals arranged toward the receptacle interior must be affixed to the shaft housing by an additional holder. A further disadvantage of this shaft guide known in the prior art is that both ball bearings on the end of the shaft guide part facing away from the receptacle interior are arranged in close proximity to each other. As the bag or the receptacle moves, the seals between the shaft housing and the shaft guide part may be subject to uneven stress.

Furthermore, a receptacle in the form of a flexible bag with a mixing device comprising a longitudinally adjustable mixing shaft is known in the prior art from DE 10 2009 018 209 A1, in which the mixing shaft is in the form of a telescoping shaft which is slidable in its longitudinal direction in a telescoping manner.

An object of the present invention is to improve the receptacles known in the prior art with a shaft housing for guiding a shaft through a wall in such a way that on the one hand the intrusion of wear debris from the seals into the receptacle, and on the other hand the uneven stress on the seals can be avoided economically.

SUMMARY

The object is achieved in that the shaft housing has the form of an annular cap towards the receptacle interior and has an inner wall spaced apart from the outer wall, said inner wall being connected to the outer wall of the shaft housing via an inner end face facing the receptacle interior; the shaft guide part, at its end facing the receptacle interior, has an outer surface separated by a gap from the inner wall of the shaft housing; the shaft guide part has an annular wall spaced apart from and parallel to its outer surface, which annular wall reaches over the free end of the inner wall of the shaft housing in the form of a cap; the annular wall is sealed in relation to the inner wall of the shaft housing on the one end and in relation to the outer wall of the shaft housing on the other end by at least one seal each; and the shaft guide part is mounted in the shaft housing by means of a first ball bearing in the form of a radial ball bearing and by means of a second ball bearing in the form of an axial ball bearing.

As a result of the shaft housing being in the form of an annular cap, wear debris from the seals is reliably prevented from intruding into the receptacle interior. At the same time, this is achieved economically without the use and mounting of an additional part. As a result of the housing part being in the form of an annular cap, an axial ball bearing, on which the shaft guide part with its annular wall arranged parallel to the outer surface in an axial direction can be supported, can be arranged in the housing part. The second, spaced radial ball bearing in combination with the axial ball bearing leads to uniform stress on the seals even when a receptacle in the form of a flexible bag is in motion. Sealing the annular wall relative to the inner wall of the shaft housing, on the one hand, and relative to the outer wall of the shaft housing, on the other hand, with at least one seal each, leads to a kind of labyrinth seal, which has proven to be especially advantageous.

According to a embodiment of the invention, the annular wall of the shaft guide part is sealed relative to the inner wall of the shaft housing in the longitudinal direction of the shaft by means of two seals arranged one behind the other. The seals arranged immediately behind one another increase the tightness of the seal by means of their additional labyrinth effect.

According to another embodiment of the invention, the seals take the form of radial shaft sealing rings with at least one sealing lip. In good seals, friction is diminished by the arrangement of sealing lips, which in turn reduces any possible wear debris.

According to another embodiment of the invention, the shaft guide part is permanently attached to a shaft extending into the receptacle interior. On the one hand, the permanent attachment between the shaft guide part and the shaft prevents sealing problems between the shaft guide part and the shaft; however, it introduces a disadvantage in that the shaft can no longer slide longitudinally relative to the guide part.

According to another embodiment of the invention, the shaft guide part has an opening to receive a shaft extending into the receptacle interior. The shaft extending into the receptacle interior may be in the form of a shaft which is encased at least in sections by a bellows that creates a seal, and which is connected to the shaft guide part at its end facing the shaft housing.

The use of a bellows reliably solves the sealing problem between the guide part and the shaft.

According to another embodiment of the invention, the shaft is in the form of multiple shaft segments arranged in a specified sequence, where the shaft segments are connected to a retaining element in such a way that when they are separated, they cannot be lost. The retaining element may be, for instance, a cord, so that the shaft is comprised of separable but non-detachable individual parts.

According to another embodiment of the invention, the shaft takes the form of a telescoping shaft.

On the one hand, the telescoping shaft extending into the receptacle interior increases flexibility; on the other hand, as shown above, the use of the bellows reliably solves the sealing problem between the guide part and the shaft.

According to another embodiment of the invention, the end of the shaft facing away from the shaft housing is guided through a guide arranged on the receptacle floor. The guide on the receptacle floor also contributes to even stress on the shaft and therefore to improve the seal between the shaft and the shaft housing.

According to another embodiment of the invention, the guide consists of a fixed guide part arranged on the receptacle floor and a rotatable receiving part for the end of the shaft, where at least one ball bearing is arranged between the receiving piece and the guide. The arrangement of the ball bearing reduces friction and the arrangement of the receiving part facilitates mounting.

According to another embodiment of the invention, the shaft takes the form of an agitator shaft with at least one agitator, where the free, outer end of said agitator shaft can be coupled to the drive shaft of a drive.

The receptacle may be designed to be a single-use bioreactor with flexible walls.

Additional features and advantages of the invention are evident from the following special description and the drawings.

DETAILED DESCRIPTION

Figure 1:
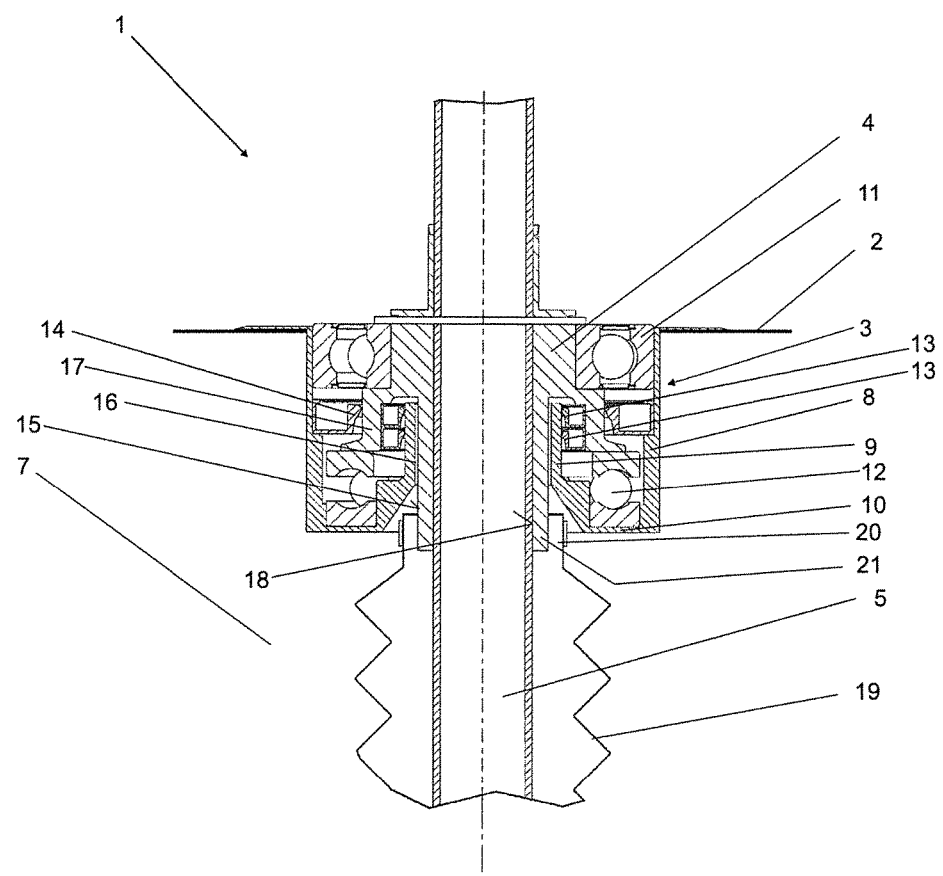
FIG. 1 a side view in cross-section and detail of a receptacle with a shaft housing, shaft guide part, shaft and bellows in an enlarged depiction of Detail I of FIG. 2.
Figure 2:
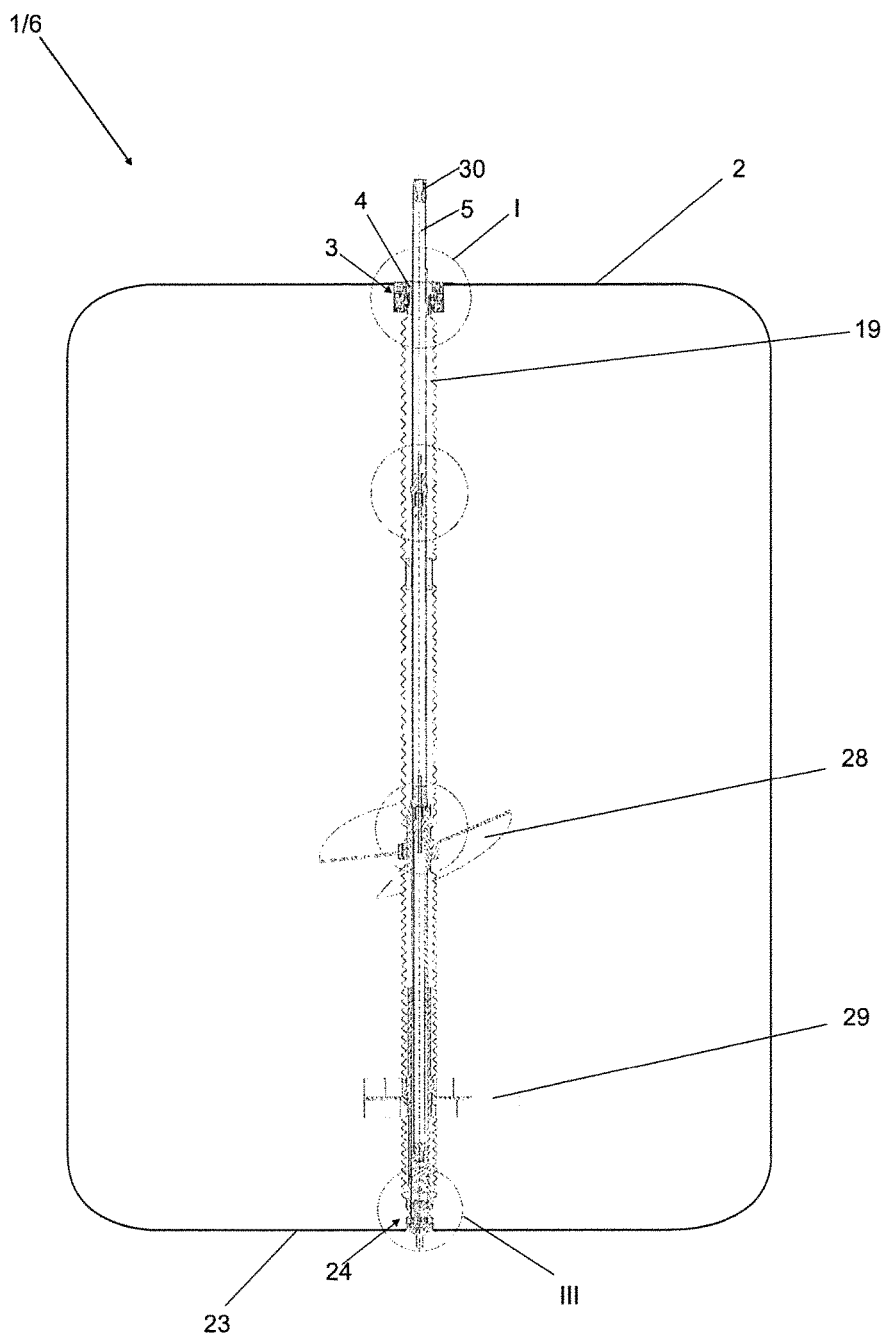
FIG. 2 a side view in cross-section of a container in the form of a bioreactor with shaft housing, shaft guide part, shaft in the form of an agitator shaft with bellows and two agitators.
Figure 3:
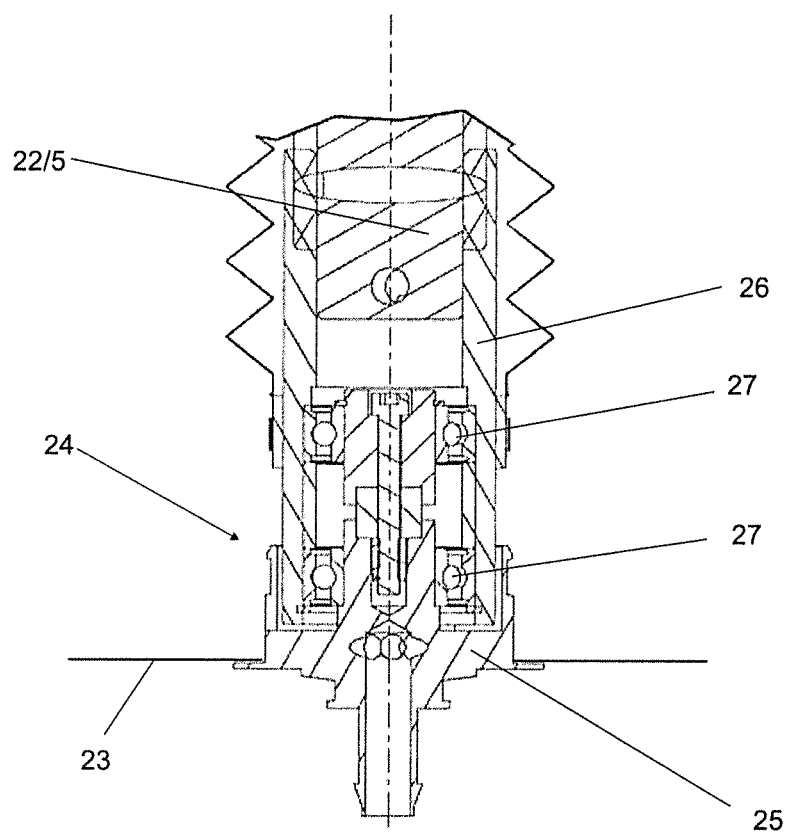
FIG. 3 an enlarged depiction of Detail section III of FIG. 2.

A receptacle 1 consists essentially of a wall 2, a shaft housing 3, a shaft guide part 4 and a shaft 5.

The receptacle 1 has a wall 2, which in the exemplary embodiment is in the form of a flexible wall of a bioreactor 6. The upper end of the flexible wall 2 is firmly attached to the shaft housing 3 in the vertical direction to guide the shaft 5.

The shaft housing 3 has the form of an annular cap towards the receptacle interior 7 and has a vertical inner wall spaced apart from its vertical outer wall 8, said inner wall being connected to the outer wall of the shaft housing 3 by way of an approximately horizontal end face 10 facing the receptacle interior 7. The shaft 5 is mounted in the shaft housing 3 via a shaft guide part 4 by way of ball bearings 11, 12 and sealed relative to the shaft housing by means of seals 13, 14. The shaft guide part 4, at its end facing the receptacle interior 7, has a vertical outer surface 15 separated by a gap 16 from the inner wall 9 of the shaft housing 3. Spaced apart from and parallel to its outer surface 15, the shaft guide part 4 has an annular wall 17 which reaches over the free end of the inner wall 9 of the shaft housing 3 in the form of a cap. The annular wall 17 is sealed relative to the inner wall 9 of the shaft housing 3, on the one hand, and relative to the outer wall 8 of the shaft housing 3, on the other hand, by at least one seal 13, 14 each. In the exemplary embodiment, the annular wall 17 is sealed relative to the inner wall 9 by two first seals 13 arranged vertically one behind the other. The annular wall 17 is sealed toward the outer wall 8 of the shaft housing 3 by means of a second seal 14. The shaft guide part 4 is mounted in the shaft housing 3 vertically at the top by the first ball bearing 11 which is in the form of a radial ball bearing, and vertically at the bottom by means of the second ball bearing 12 which is in the form of an axial ball bearing.

The seals 13, 14 are in the form of radial shaft sealing rings, each with a sealing lip. In the exemplary embodiment, the shaft guide part 4 has an opening 18 or channel to receive the shaft 5 extending into the receptacle interior 7. The shaft 5 is encased with a first bellows 19 to seal it toward the shaft housing 3. The bellows 19 is connected at its top end 20 to the free end 21 of the shaft guide part 4. According to the exemplary embodiment, the shaft 5 is guided, at its lower end 20 facing away from the shaft housing 3, in a guide 24 arranged on the receptacle floor 23. The guide 24 consists of a fixed guide part 25 arranged on the receptacle floor 23 and a rotatable receiving part 26 into which the lower end 22 of the shaft 5 can be placed. The receiving part 26 is mounted by means of two ball bearings 27 which are both in the form of radial ball bearings in the exemplary embodiment. In the exemplary embodiment, the shaft 5 is in the form of an agitator shaft with a first agitator 28 which is in the form of a segmented blade agitator, and a second agitator 29 which is in the form of a six-blade agitator.

A drive (not shown) can be coupled to the outer free end 30 of the shaft 5.

Of course, the embodiments discussed in the specific description and shown in the figures are merely illustrative exemplary embodiments of the present invention. In light of this disclosure, a person skilled in the art is given a wide range of possible variations.

LIST OF REFERENCE NUMBERS

1 Receptacle
2 Wall of 1
3 Shaft housing
4 Shaft guide part
5 Shaft
6 Bioreactor
7 Receptacle interior
8 Vertical outer wall of 3
9 Vertical inner wall of 3
10 Horizontal end face of 3
11 First ball bearing, radial
12 Second ball bearing, axial
13 Seal (2)
14 Seal (2)
15 Vertical outer surface of 4
16 Gap
17 Annular wall of 4
18 Receiving opening of 4
19 First bellows
20 Upper end of 19
21 Free end of 4
22 Lower end of 5
23 Receptacle floor of 1
24 Guide
25 Guide part of 24
26 Receiving part of 24
27 Ball bearing of 24
28 First agitator
29 Second agitator
30 Outer free end of 5

The invention claimed is:
1. A receptacle (1), comprising:
a shaft housing (3) for guiding a shaft (5) through a wall (2) into a receptacle interior (7), the shaft (5) being mounted in the shaft housing (3) via a shaft guide part (4) by way of ball bearings (11, 12) and being sealed relative to the shaft housing (3) by seals (13, 14), wherein:

the shaft housing (3) has the form of an annular cap towards the receptacle interior (7) and has an inner wall (9) spaced apart from the outer wall (8), said inner wall (9) being connected to the outer wall (8) of the shaft housing (3) via an inner end face (10) facing the receptacle interior (7);

the shaft guide part (4) has an end (21) facing the receptacle interior (7) the end of the shaft guide part (4) having an outer surface (15) separated by a gap (16) from the inner wall (9) of the shaft housing;

the shaft guide part (4) has an annular wall (17) spaced apart from and parallel to its outer surface (15), the annular wall extends over the free end of the inner wall (9) of the shaft housing (3) in the form of a cap; and the annular wall (17) is sealed in relation to the inner wall (9) of the shaft housing (3) on the one end and in relation to the outer wall (8) of the shaft housing (3) on the other end by at least one seal (13, 14) each;

and the shaft guide part (4) is mounted in the shaft housing (3) by a first ball bearing (11) in the form of a radial ball bearing and by a second ball bearing (12) in the form of an axial ball bearing.

2. The receptacle of claim 1, wherein the annular wall (17) of the shaft guide part (4) is sealed toward the inner wall (9) of the shaft housing (3) in a longitudinal direction of the shaft (5) by two seals arranged one behind the other.

3. The receptacle of claim 2, wherein:
the seals (13, 14) are radial shaft sealing rings, each of which has at least one sealing lip.

4. The receptacle of claim 1, wherein:
the shaft guide part (4) is permanently connected to the shaft (5) extending into the receptacle interior (7).

5. The receptacle of claim 1, wherein:
the shaft guide part (4) has an opening (18) or canal to receive the shaft (5) extending into the receptacle interior (7).

6. The receptacle of claim 5, wherein:
the shaft (5) extending into the receptacle interior (7) is encased at least in sections by a bellows (19) that creates a seal, and that is connected to the shaft guide part (4) at its end (20) facing the shaft housing (3).

7. The receptacle of claim 1, wherein:
the shaft (5) comprises multiple shaft segments arranged in a specified sequence, and
the shaft segments are not detachable when they are separated because of a retaining element.

8. The receptacle of claim 1, wherein that the shaft (5) is a telescoping shaft.

9. The receptacle of claim 1, wherein:
the shaft (5) is guided at its lower end (22) facing away from the shaft housing (3) in a guide (24) arranged on the receptacle floor (23).

10. The receptacle of claim 9, wherein:
the guide (24) comprises a fixed guide part (25) arranged on the receptacle floor (23) and a rotatable receiving part (26) for the end (22) of the shaft (5), and that at least one ball bearing (27) is arranged between the receiving part (26) and the guide (24).

11. The receptacle of claim 1, wherein the shaft (5) is an agitator shaft with a free outer end and at least one agitator (28) spaced from the free outer end, and the free outer end (30) of said agitator shaft being configured to be coupled to a drive shaft of a drive.

12. The receptacle of claim 1, wherein:
the receptacle (1) is a single-use bioreactor with flexible walls.

* * * * *